US00PP09043P

United States Patent [19]

Kordes

[11] Patent Number: Plant 9,043

[45] Date of Patent: Jan. 17, 1995

[54] HYBRID TEA ROSE PLANT NAMED KORCRISETTE

[75] Inventor: Wilhelm Kordes, Sparrieshoop, Germany

[73] Assignee: Bear Creek Gardens, Inc., Medford, Oreg.

[21] Appl. No.: 241,500

[22] Filed: May 12, 1994

[51] Int. Cl.[6] ..... A01H 5/00

[52] U.S. Cl. ..... Plt./17

[58] Field of Search ..... Plt. 11, 16, 17, 20

*Primary Examiner*—Howard J. Locker

*Attorney, Agent, or Firm*—Klarquist Sparkman Campbell Leigh & Whinston

[57] ABSTRACT

A Hybrid Tea rose plant having excellent cut flower vase life; high cut-flower production; bright orange flowers; thick, leathery petals, and attractive, high-centered flowers.

1 Drawing Sheet

The present invention relates to a new and distinct variety of rose plant of the Hybrid Tea class which was originated by me by crossing two unpatented, unnamed seedlings.

The primary objective of this breeding was to produce a new rose variety having the high cut-flower production, excellent vase life and good flower form of the male parent combined with the good production of cut flowers and longer stem length of the female parent. The objective was substantially achieved, along with other desirable improvements, as evidenced by the following unique combination of characteristics that are outstanding in the new variety and that distinguish it from its parents, as well as from all other varieties of which I am aware:

1. Excellent production of straight, strong, flowering stems;
2. Bright orange flower color;
3. Thick, leathery petals;
4. Excellent vase life; and
5. Attractive, high-centered flower form.

Asexual reproduction of this new variety by budding, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—An unnamed seedling (unpatented).

*Pollen parent.*—An unnamed seedling (unpatented).

Classification:

*Botanical.*—*Rosa hybrida.*

*Commercial.*—Hybrid Tea.

FLOWER

Observations made from specimens grown in a greenhouse environment at Sparrieshoop, Germany, and Somis, Calif., from October, 1993, through March, 1994.

Blooming habit: Continuous.

Bud:

*Size.*—1¼ inches long when the petals start to unfurl.

*Form.*—The bud form is long, pointed ovoid.

*Color.*—When sepals first divide, bud color is Red Group 41B. When half blown, the upper sides of the petals are Orange-Red Group 33A; and the lower sides of the petals are Red Group 41B.

*Sepals.*—Color: Green Group 138B. Surface texture: Covered in fine hairs. There are three normally to heavily appendaged sepals. There are two unappendaged sepals with hairy edges.

*Receptacle.*—Color: Green Group 143C. Shape: Funnel. Size: Broad (¼ inch wide×⅜ inch long). Surface: Smooth.

*Peduncle.*—Length: Medium (2 inches). Surface: Smooth. Color: Light green. Strength: Stiff, erect, heavy.

Bloom:

*Size.*—Medium. Average open size is 3½ inches.

*Borne.*—Singly.

*Stems.*—Medium length, strong. Average length is about 18–22 inches. High production of stems throughout year with production of about 210 to 220 flowers per square meter.

*Form.*—When first open: High-centered. Permanence: Retains its form to the end, outer petals curl back, quill fashion.

*Petalage.*—Number of petals under normal conditions: 25–30.

*Color.*—The upper side of the petals is Orange-Red Group 33A. The reverse side of the petals is Red Group 41B. The base of each petal has a small (⅛ inch×3/16 inch) Yellow Group 1D half-moon at the point of attachment. The major color on the upper side is Orange-Red Group 33A.

*Variegations.*—Occasional white streak on the guard petals.

*Discoloration.*—The general tonality at the end of the first day: No change. At the end of the third day, no change. By day 7 on the plant, there is some fading to Orange-Red Group 33B.

*Fragrance.*—Slight.

Petals:

*Texture.*—Thick, leathery.
*Shape.*—Round.
*Form.*—Edges moderately quilled.
*Arrangement.*—Imbricated with a few small petaloids in the center.
*Persistence.*—Drop off cleanly.
*Lastingness.*—On the plant: Very long (10–12 days). As a cut flower: Very long (14–16 days).

Reproductive parts:
*Anthers.*—Size: Small. Quantity: Many. Color: Yellow. Arrangement: Regular around styles.
*Filaments.*—Color: Reddish.
*Pollen.*—Color: Lemon yellow.
*Styles.*—Color: Reddish.
*Stigmas.*—Color: Greenish white.

Form: Bush.

Growth: Vigorous, upright, branching. Height at maturity (one year), in the greenhouse, is 5 feet, and the width is 3½ feet.

Foliage:
*Number of leaflets on normal mid-stem leaves.*—5.
*Size.*—Medium (5 inches long×3½ inches wide).
*Quantity.*—Abundant.
*Color.*—New foliage: Under Side: Greyed-Orange Group 176B. Upper side: Greyed-Orange Group 176B. Old foliage: Under Side: Green Group 139C. Upper Side: Green Group 137A.

Leaflets:
Shape.—Pointed oval.
*Texture.*—Upper side: Leathery.
*Edge.*—Serrated.

*Serration.*—Single, small.
*Petiole rachis.*—Color: Green.
*Petiole underside.*—Smooth, usually with three small prickles.
*Stipules.*—Medium (½ inch), serrated, bearded.
*Disease resistance.*—Resistant to mildew under normal growing conditions at Somis, Calif. Other fungal diseases not checked.

Wood:
*New wood.*—Color: Light green. Bark: Smooth.
*Old wood.*—Color: Green. Bark: Smooth.

Prickles:
*Quantity.*—On main canes from base: Ordinary to few. On laterals from main canes: Ordinary to few.
*Form.*—Short (⅛ inch), straight to slightly hooked downward.
*Color when young.*—Red.

Small prickles:
*Quantity.*—On main stalks: None. On laterals: None.

I claim:

1. A new and distinct variety of rose plant of the Hybrid Tea class, substantially as herein shown and described, characterized particularly as to novelty by the unique combination of the excellent vase life of its cut flowers; high cut-flower production; bright orange flowers; thick, leathery petals, and attractive, high-centered flower form.

* * * * *

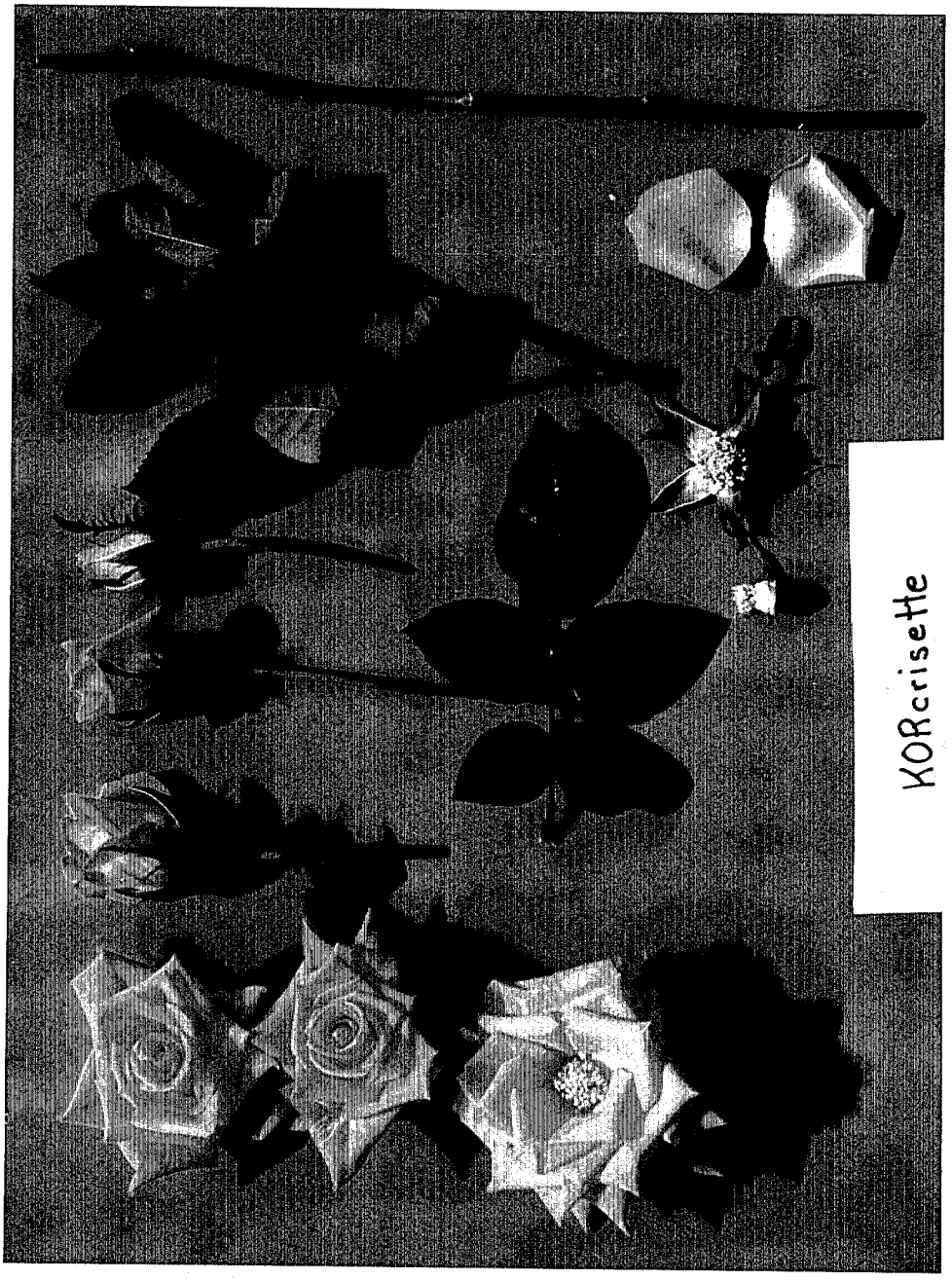
KORcrisette